US012781175B2

(12) United States Patent
Henry

(10) Patent No.: US 12,781,175 B2
(45) Date of Patent: Nov. 3, 2026

(54) APPARATUS, KIT AND A METHOD FOR THE PROVISION AND USE OF ELECTROMAGNETIC FIELDS WITH RESPECT TO A BIOREACTION

(71) Applicant: St Andrews Pharmaceutical Technology Limited, St Andrews Fife (GB)

(72) Inventor: William J. Henry, St Andrews Fife (GB)

(73) Assignee: St Andrews Pharmaceutical Technology Limited, Oxfordshire (GB)

( * ) Notice: Subject to any disclaimer, the term of this patent is extended or adjusted under 35 U.S.C. 154(b) by 649 days.

(21) Appl. No.: 17/917,143

(22) PCT Filed: Apr. 29, 2021

(86) PCT No.: PCT/GB2021/051037
§ 371 (c)(1),
(2) Date: Oct. 5, 2022

(87) PCT Pub. No.: WO2021/220004
PCT Pub. Date: Nov. 4, 2021

(65) Prior Publication Data

US 2023/0159879 A1 May 25, 2023

(30) Foreign Application Priority Data

Apr. 30, 2020 (GB) ..................................... 2006419
Nov. 27, 2020 (GB) ..................................... 2018710

(51) Int. Cl.
*C12M 1/42* (2006.01)
*C12M 1/00* (2006.01)
*C12M 1/06* (2006.01)

(52) U.S. Cl.
CPC ............ *C12M 35/02* (2013.01); *C12M 23/14* (2013.01); *C12M 23/22* (2013.01); *C12M 23/34* (2013.01); *C12M 27/02* (2013.01)

(58) Field of Classification Search
None
See application file for complete search history.

(56) References Cited

U.S. PATENT DOCUMENTS

2006/0024822 A1* 2/2006 Chang .................... C12M 29/00 435/325
2006/0223155 A1 10/2006 Streeter
(Continued)

FOREIGN PATENT DOCUMENTS

CN 103842028 A 6/2014
CN 110358679 A 10/2019
(Continued)

OTHER PUBLICATIONS

McKeen, Laurence, Effect of Sterilization Methods on Plastics and Elastomers (4th Edition), Elsevier. Retrieved from knovel.com, 2018. (Year: 2018).*
(Continued)

*Primary Examiner* — Michael A Marcheschi
*Assistant Examiner* — Ashley Lopezlira
(74) *Attorney, Agent, or Firm* — Conley Rose, P.C.

(57) ABSTRACT

A kit and a method for improving the quality, acceleration of change in and or improving the yield from a bioreaction of a bioreaction mixture. The bioreaction mixture is typically held in an inner space in a vessel, such as a biomanufacturing vessel, with means for movement of the bioreaction mixture and one or more modules are provided to emit one or more electromagnetic fields to which the bioreaction mixture is exposed over a period of time.

34 Claims, 11 Drawing Sheets

(56) References Cited

U.S. PATENT DOCUMENTS

Figure 1A:
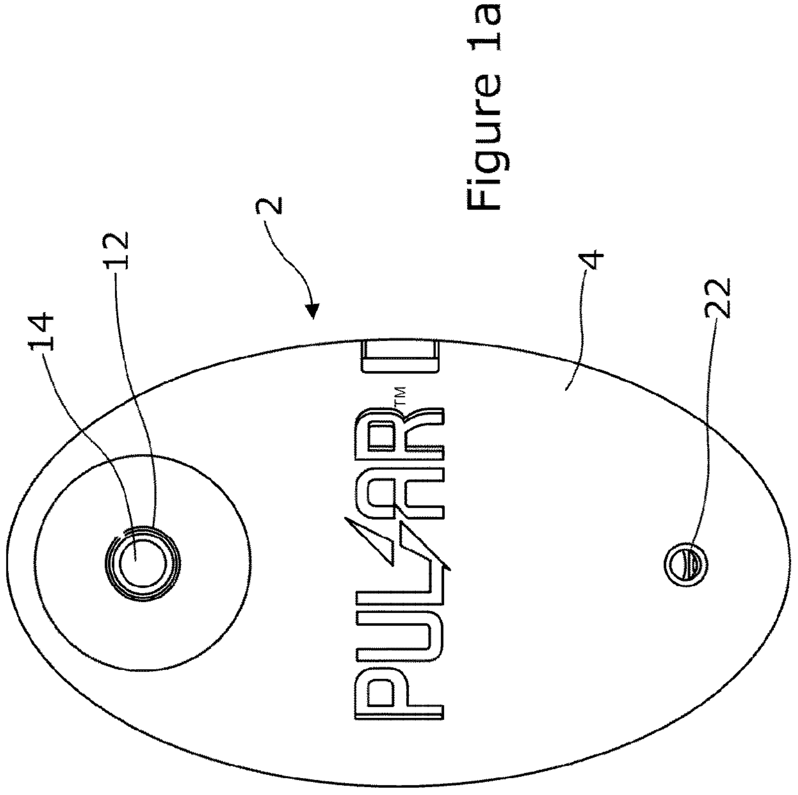
Figure 1B:
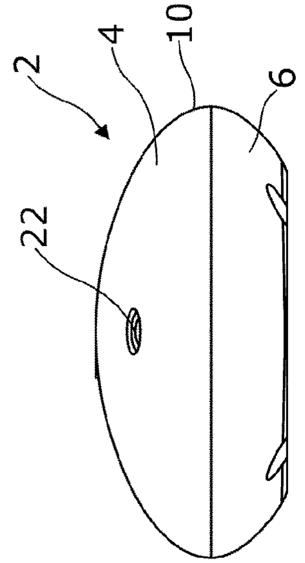
Figure 1C:
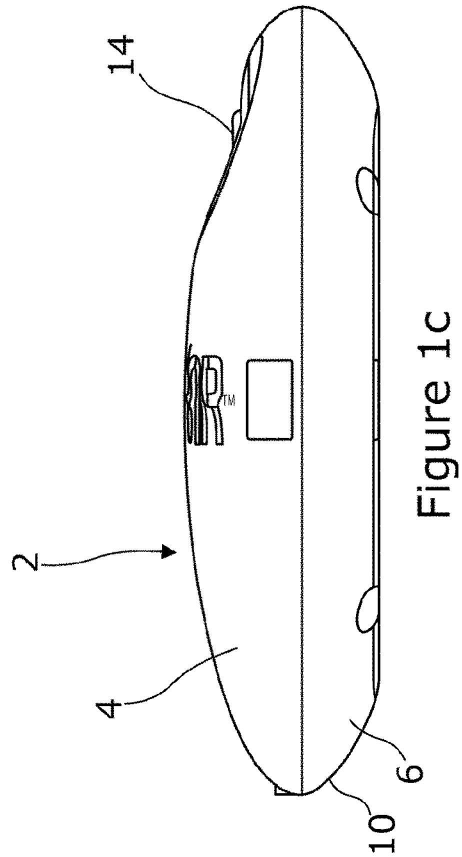
Figure 1D:
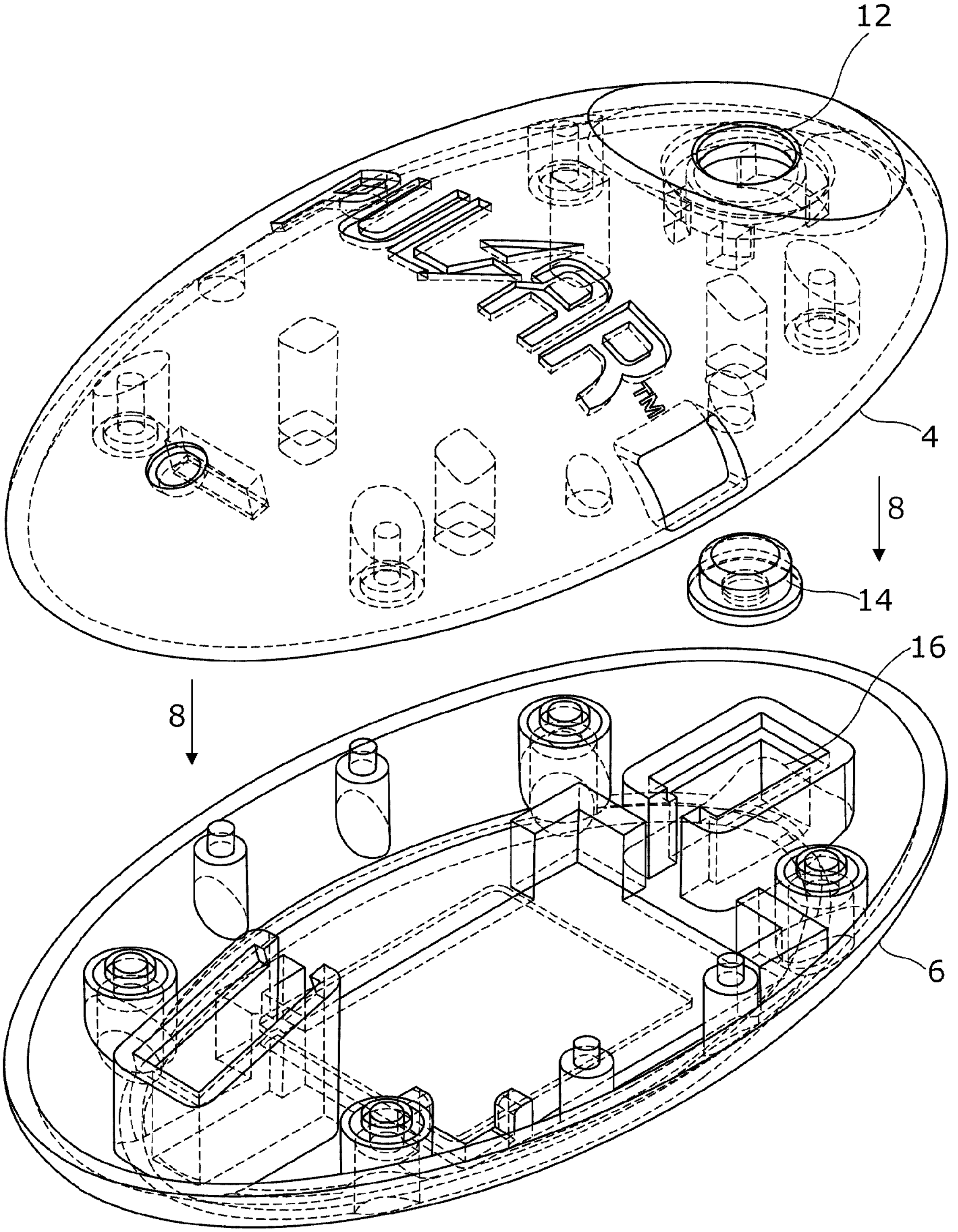

| | | | | |
|---|---|---|---|---|
| 2010/0005711 | A1 | 1/2010 | McNeff | |
| 2013/0164812 | A1 | 6/2013 | Eckelberry et al. | |
| 2015/0099274 | A1 * | 4/2015 | Axelrod | C12M 41/34 435/39 |
| 2018/0296786 | A1 | 10/2018 | Barlow | |
| 2019/0309241 | A1 | 10/2019 | Ott et al. | |
| 2019/0309255 | A1 * | 10/2019 | Ott | C12M 43/00 |
| 2020/0283710 | A1 * | 9/2020 | Leupold | C12M 23/22 |
| 2023/0113048 | A1 * | 4/2023 | Boudier | C12M 21/02 435/292.1 |

FOREIGN PATENT DOCUMENTS

| | | | | |
|---|---|---|---|---|
| WO | WO-2013055819 A1 * | 4/2013 | | C12N 13/00 |
| WO | 2019057508 | 3/2019 | | |
| WO | 2019234442 A1 | 12/2019 | | |

OTHER PUBLICATIONS

Foreign Communication from a Related Counterpart Application, Brazil Search Report and Opinion dated May 16, 2025, Brazil Application No. BR112022015914-5 filed on Apr. 29, 2021.
Foreign Communication from a Related Counterpart Application, Brazil Technical Examination Report dated Mar. 12, 2026, Brazil Application No. BR112022015914-5 filed on Apr. 29, 2021.
Foreign Communication from a Related Counterpart Application, Mexico Office Action dated Jun. 18, 2025, Mexico Application No. MX/a/2022/009918 filed on Aug. 11, 2022.
Foreign Communication from a Related Counterpart Application, United Arab Emirates Office Action dated Oct. 8, 2024, United Arab Emirates Application No. P6002153/2022 filed on Oct. 17, 2022.
Foreign Communication from a Related Counterpart Application, Chile Search Report dated Apr. 4, 2024, Chile Application No. 202202805 filed on Oct. 12, 2022.
Foreign Communication from a Related Counterpart Application, Austrailia Examination Report dated Mar. 6, 2026, Australia Application No. 2021264036 filed on Apr. 29, 2021.
Foreign Communication from a Related Counterpart Application, Canada Examination Search Report and Opinion dated Aug. 18, 2023, Canada Application No. 3163015 filed on Apr. 29, 2021.
Foreign Communication from a Related Counterpart Application, Canada Examination Search Report and Opinion dated Apr. 9, 2025, Canada Application No. 3163015 filed on Apr. 29, 2021.
Foreign Communication from a Related Counterpart Application, Korea Request of the Submission of an Opinion dated Sep. 25, 2025, Korea Application No. 2022-7038240 filed on Nov. 1, 2022.
Foreign Communication from a Related Counterpart Application, China Office Action dated Apr. 16, 2026, China Application No. 202180019076.7 filed on Apr. 29, 2021.
Foreign Communication from a Related Counterpart Application, China Search Report dated Sep. 13, 2025, China Application No. 202180019076.7 filed on Apr. 29, 2021.
Foreign Communication from a Related Counterpart Application, Japan Notification of Reasons for Refusal dated May 27, 2025, Japan Application No. 2022-565990 filed on Apr. 29, 2021.

* cited by examiner

APPARATUS, KIT AND A METHOD FOR THE PROVISION AND USE OF ELECTROMAGNETIC FIELDS WITH RESPECT TO A BIOREACTION

CROSS-REFERENCE TO RELATED APPLICATIONS

This United States application is the National Phase of PCT Application No. PCT/GB2021/051037 filed 29 Apr. 2021, which claims priority to British Patent Applications No. 2006419.2 filed 30 Apr. 2020 and No. 2018710.0 filed 27 Nov. 2020, each of which is incorporated herein by reference.

The invention to which this application relates is the application of one or more electromagnetic fields, such as a series of pulsed electromagnetic fields (PEMF), (which can also be referred to as Digital sequences of Electromagnetism), to a material in the form of a bioreaction mixture to achieve an improvement in relation to the same, such as an improved yield, and/or an acceleration in the change of condition of the material and/or an improvement in the quality of the same.

The changes, enhancement and/or acceleration in condition which can be influenced are particularly relevant in the bioreaction of a bioreaction mixture, and examples of which are metabolic productivity of biosystems such as fermentation and cell-culture biosystems.

In order for the application of the one or more electromagnetic fields to be effective on a relatively large scale in terms of several litres of bioreaction mixture, it is preferred to be able to ensure that the one or more electromagnetic fields are applied in a reliable and repeatable manner in order to ensure that the beneficial effect is achieved substantially uniformly and that all of the bioreaction mixture is exposed to the electromagnetic fields which are emitted to a similar extent. There is also a need for the effect and enhancements to be achieved in a repeatable and reliable manner and for the process to be preferably controllable by non-skilled personnel, thereby maximising the possibility of the apparatus and method being used in relatively large scale manufacturing environments rather being solely a laboratory based process as is conventionally the case with many bioreaction techniques.

It is known to provide the bioreaction mixture within a vessel and, while there are known systems for applying a magnetic field to a bioreaction mixture, these known systems most typically include one or more coils which are located at the top and/or bottom, within the vessel and it is found that problems exist with the ability of this form of apparatus to be able to provide a uniform treatment of the bioreaction mixture within the vessel and also to achieve the required change in condition of the bioreaction mixture within a time scale which is commercially acceptable. The applicant has, in their co-pending application, WO2019/234442, the content of which is incorporated herein by reference, disclosed a further form of apparatus.

An aim of the present invention is therefore to provide a solution to the above-mentioned problems and to provide apparatus and a method which is reliable and allows relatively uniform treatment of a bioreaction mixture to allow the quality, yield and/or speed of the change of the bioreaction mixture to be improved in comparison to conventional apparatus and methods. A further aim is to allow the same to be achieved in a reliable and uniform manner and on a scale which is suited to commercial implementation of batch production.

A further aim is to provide apparatus and a method which is non-invasive of the bioreaction mixture.

A further aim of the present invention is to provide apparatus and a method which allows the effective application of the one or more electromagnetic fields to the bioreaction mixture in a manner which is relatively easily and reliably repeatable and which preferably can be used in conjunction with a vessel in the form of a bioreactor vessel in which the material is held.

In a first aspect of the invention there is provided apparatus for improving the yield and/or acceleration and/or quality of a bioreaction, the apparatus comprising; a vessel formed from a plurality of walls comprising at least one side wall and a base forming an internal space for holding a bioreaction mixture, means to cause movement of said bioreaction mixture, and one or more modules, said module comprising a housing and a transmitter disposed within said housing, said transmitter being capable of emitting one or more electromagnetic fields, wherein the one or more modules are proximal to at least one portion of said walls which is made from a material which is substantially transparent to said one or more electromagnetic fields, and/or wherein the one or more modules are disposed in the said internal space.

In one embodiment the one or more modules are disposed in said bioreaction mixture in said internal space. In one embodiment said housing comprises a liquid-tight cover made of a plastic or glass material.

In one embodiment the said plurality of walls includes a lid of the vessel.

In one embodiment the said lid includes a portion made from a material which is substantially transparent to said one or more electromagnetic fields and said one or more modules are positioned proximal thereto.

In one embodiment the said at least one portion made from a material substantially transparent to said one or more electromagnetic fields is made from a material which is non-metallic, such as plastic or glass.

In one embodiment the said means to cause movement are electrical and/or mechanical movement means. In one embodiment the movement means are in the form of any, or any combination of; an agitator within the vessel internal space; an agitator external to the vessel internal space; a means for imparting vibration to the vessel and/or bioreaction mixture; a wave generator; an input flow of material into the internal space and/or an output flow of material from said internal space.

In one embodiment one or more of said modules are included with, attached to or integral with the said agitator.

In one embodiment the agitator within the internal space is a stirrer, a propellor, an impellor, and/or a gas-sparger.

In one embodiment the said means to cause movement includes one or more components of the bioreaction mixture.

In one embodiment the said means to cause movement move said bioreaction mixture so as to periodically expose substantially all of said bioreaction mixture to the said one or more electromagnetic fields emitted from the said one or more modules and/or to retain cells in the said bioreaction mixture substantially in suspension in the said bioreaction mixture. This ensures that even though the electromagnetic fields which are emitted do not extend throughout the bioreaction mixture, the bioreaction mixture will move through the zones of electromagnetic field emissions and therefore provide exposure of all of the bioreaction mixture to the electromagnetic fields over time.

In one embodiment the apparatus includes a frame and the vessel is formed of a bag made from a flexible, resilient, plastic material and is supported by the frame. Typically, in this embodiment, the one or more modules are attached to the frame and/or the sheet material.

In one embodiment the said electromagnetic fields emitted by the transmitter are a series of pulsed electromagnetic fields (PEMFS).

In one embodiment the apparatus further comprises a control means for controlling the form of the said one or more electromagnetic fields emitted from the one or more modules.

In one embodiment the said one or more electromagnetic fields are emitted at a frequency so as to cause rotation of the molecular dipole of water contained in the bioreaction mixture.

In one embodiment the control means control emission of the one or more electromagnetic fields at a frequency or frequencies in the range of 2.4 GHz to 2.5 GHz.

In one embodiment the electromagnetic fields are emitted at a plurality of different frequencies in a random sequence during the period of time of emission of the one or more electromagnetic fields.

In one embodiment when there are two or more modules, the one or more electromagnetic fields emitted therefrom are emitted in a synchronised manner.

Typically the control means is integral to the module, vessel or the frame.

In one embodiment the apparatus includes a holder and said one or more modules are located on said holder and said holder is locatable with the vessel.

In one embodiment the one or more modules include a rechargeable power source.

In one embodiment the said transmitter provides wireless short-range communication of the electromagnetic fields.

In one embodiment the apparatus comprises one or more locators for locating the one or more modules proximal to, in one or more walls or within the vessel. Typically the one or more locators comprise one or more of a hook, a hook-and-loop fastener, an adhesive patch, a threaded locator, a magnet, or any combination thereof.

In one embodiment, when the one or more modules are disposed in the internal space and in the bioreaction mixture held therein, the one or more modules further comprise at least one buoyancy portion for holding the one or more modules at a depth in the bioreaction mixture, when the bioreaction mixture comprises a liquid.

In one embodiment when there are two or more modules, at least one of the modules has a buoyancy portion of a selected form to retain the same at a different depth in the bioreaction mixture than another module or modules in the bioreaction mixture when the bioreaction mixture is a liquid.

In one embodiment each of the two or more modules in a group of modules is provided with a buoyancy portion of a selected form so as to retain the said modules at different respective depths in the bioreaction mixture when the bioreaction mixture comprises a liquid.

In one embodiment the vessel includes one or more hollow elongated members which extend from the at least one wall, the base, and/or the lid such that the one or more elongated members are not in fluid communication with the internal space, and wherein at least one of the one or more hollow elongated members comprises the at least one portion made from a material which is transparent to electromagnetic fields.

In one embodiment the one or more modules are two or more modules, and each of the two or more modules is located at a node of another module.

In one embodiment the said adjacent modules are spaced at a distance of half a wavelength of the frequency of the emitted electromagnetic fields. In one embodiment the said modules are located in the array so that there is a spacing within a range of 5 and 10 cm between adjacent modules in the array.

In one example, the wavelength of an electromagnetic field of a frequency of 2.45 GHz is approximately 12.2 cm and hence the modules are placed 6.1 cm apart. The wavelength paths cross at the module locations and avoids interference between the modules and so these spacings can be used when locating the modules in an array of modules.

There is therefore provided apparatus for the application of one or more electromagnetic fields to a bioreaction mixture for a period of time using at least one vessel in which the said bioreaction mixture is located and at least one transmitter to emit one or more of said electromagnetic fields therefrom and into one or more zones of the internal space of the vessel and into and through which said one or more zones the bioreaction mixture is moved by movement means so as to ensure that substantially all of the bioreaction mixture is substantially uniformly exposed to the electromagnetic fields in the one or more zones.

Typically the transmitter is provided as part of a module and one or more modules can be located at least partially in said bioreaction mixture and/or proximal to one or more walls of the said vessel during the emission of said electromagnetic fields and said modules are controlled to emit said electromagnetic fields at a frequency, or a range of frequencies, continuously, or in pulses, during said period of time.

Typically the electromagnetic fields are emitted at a plurality of different frequencies in a random sequence during a said period of time. In one embodiment the said frequencies are in the range of 2.4-2.5 GHz. In one embodiment the specific frequencies are 2402 MHz, 2426 MHz and 2480 MHz.

In one embodiment said housing includes location means to allow the module to be located at a selected location on, or adjacent to, one or more walls of said vessel or the module may be provided integral with a wall of said vessel or in a recess or aperture therein.

In one embodiment the module or modules are provided along with at least part of the vessel as a kit and once the use of the kit has been made, the one or modules are recharged, if necessary, and re-used. Alternatively, the one or more modules may be passed for recycling, such as by return to the supplier who may then charge the same and make the modules available for subsequent use to the previous, or another user. Thus, the end user of the module or modules may be different to the supplier of said module or modules.

In one embodiment a holder for a plurality of said modules is provided which allows said modules to be located with the vessel and to be retained in a predefined spaced array.

A power source is typically provided to allow the components to be provided with sufficient power to operate for at least a predetermined period of time and switching means are provided to allow the selective operation of the module.

In one embodiment the power source is a rechargeable source provided within the module and connection to a charging facility is provided wirelessly or via a socket located on the module, and most typically when the module is not being used.

In one embodiment the specific frequency range of the said one or more electromagnetic fields is the industrial, scientific and medical (ISM) short-range radio frequency band.

In one embodiment the transmitter is capable of generating the electromagnetic field up to a distance of 15 metres.

In one embodiment the control means allow the frequency and digital sequence of the electromagnetic fields which are emitted, to correspond to the dielectric properties and/or other properties of water molecules within the said bioreaction mixture.

In one embodiment the transmission of the one or more electromagnetic fields are in one millisecond pulses in the range of 2.4-2.5 GHz at low pulse frequencies between 10 to 20 Hz such that the duty cycle is typically in the range of 1 to 2%.

In one embodiment the apparatus includes location means for nutrients which are required to be used in relation to and/or added to the bioreaction mixture in the inner space of the vessel.

Typically the one or more modules are located and controlled to create a substantially uniform strength of emission of electromagnetic fields to and into the said bioreaction mixture.

In one embodiment the number of modules, the configuration of the array of the same and/or the strength of the electromagnetic fields emitted therefrom will be selected to suit the particular usage of the modules and/or the bioreaction mixture located in the vessel at a particular time of use.

In another embodiment the location of the modules on the wall of the vessel are selected with regard to the location of the bioreaction mixture and/or nutrients within the vessel inner space so as, for example, to allow the modules to be located in intimate proximity to the nutrients and/or bioreaction mixture by locating the same on the external surface of the wall opposing the location of the nutrients or bioreaction mixture.

In one embodiment the array extends from the base of the vessel upwards to a fill level to which the bioreaction mixture can be present in the inner space of the vessel.

In one embodiment the said array extends along a single axis such as a column or row, or is provided to extend along a plurality of axes.

Typically, the modules are pre-set with respect to the particular frequency of the electromagnetic field frequency or frequencies which are emitted and typically also with a predetermined pulse frequency.

In one embodiment the module is provided as a sealed unit and access to the internal components in the housing is only provided to allow the connection of a charging connection for the power source of the module. In an alternative embodiment no charging connection is provided and the charging of the power source is performed wirelessly.

In one embodiment a change in operating control parameters for the module is received by a wireless receiver provided in the module.

In one embodiment each module has a unique identification code.

In one embodiment the use of the module is disabled until a payment has been made to the module provider, said payment made by a customer and which will then allow the module to be used, typically for a number of switching on/off functions or for a specific period of time.

In one embodiment the module control means control the frequency and digital sequence of the one or more electromagnetic field signals which are emitted so that the same correspond to and/or are in relationship with the dielectric properties and/other properties of the bioreaction mixture which is held in the vessel at that time.

In one embodiment the control means are provided in the form of an integrated circuit provided in the housing and which includes the transmitter to allow the emission of the electromagnetic fields therefrom.

In one embodiment the apparatus includes a charging and/or control unit with which the one or more modules, when not in use, are provided in electrical and/or data connection so as to allow activation and/or charging. In one embodiment the user of the modules will be able to selectively activate the modules which they are in possession of via a remote payment scheme and when payment has been made, the control unit changes the condition of one, some, or all of the modules, depending on the level of payment that has been made, to an active mode in which the electromagnetic fields can be emitted therefrom.

Typically the selective location of the modules in an array, in conjunction with agitating means allows substantially uniform exposure to the electromagnetic fields transmitted from the modules over a predetermined period of time when the type of bioreaction mixture, dimensions of the vessel, quantity of bioreaction mixture and the configuration of the array of the modules is selected accordingly.

Typically when a plurality of modules are provided in an array, the modules, in combination, act as a unitary electromagnetic field signal emitting means. In one embodiment the control means allows the synchronised and sequential emission of pulsed electromagnetic fields (PEMFS).

In one embodiment the one or more electromagnetic field signals are emitted from the array of modules for all or part of the processing of the bioreaction mixture held within the internal space of the vessel.

In one embodiment the electromagnetic fields are emitted for a predetermined period of time which is determined with reference to the particular bioreaction mixture and/or quantity of the bioreaction mixture.

In one embodiment, the duration of the application of the one or more electromagnetic fields is in the range of 30 minutes to 2 hours and which can be performed at the same time as another function, if required, such as the chilling of the bioreaction mixture. It should also be appreciated that the duration of the application of pulsed electromagnetic fields is dependent upon the type and/or quantity of the bioreaction mixture which is being treated and/or the desired end product.

When the electromagnetic fields are pulsed, the provision of the rest period between pulses ensures that the bioreaction mixture microorganisms are not overwhelmed by electromagnetic energy but instead are encouraged to increase metabolic processes and increase growth rate. It is found that this can result in an increase in expression of metabolites and a more efficient conversion of nutrients, hence increasing yields and/or decreasing production time required to achieve the desired result. Furthermore, the rest periods between the pulses can allow the activity generated in the bioreaction mixture to relax and promote homogeneity of the bioreaction mixture as clusters in the mixture are broken apart and a thermodynamically favourable open structure of the bioreaction mixture is naturally formed.

In one embodiment, the use of the apparatus in accordance with the invention provides any, or any combination, of increased productivity in the production of biofuels, cultures of genetically modified cells and organisms, insulin, monoclonal antibodies, growth hormones, interferon, interleukins, blood factor VIIa, blood factor VIII, blood factor IX, erythropoietin, gonadotrophin, glucagon, vaccine antigenic sequences, mammalian cell culture.

Typically microbial organisms in the bioreaction mixture are electrically magnetic systems and respond to changes in electromagnetism. In one embodiment in order to detect the generation of the electromagnetic fields, electronic magnetic field detectors can be utilised in the vicinity of the apparatus.

In one embodiment, the use of the electromagnetic fields is controlled so as to be used in aerobic conditions and in one embodiment, there is provided the application of electromagnetic fields to a bioreaction mixture in an aerobic environment. Although not the only use, it is envisaged that the use of the apparatus and method in aerobic conditions is of particular benefit.

In a further aspect of the invention there is provided a kit for improving the yield and/or acceleration and/or quality of a bioreaction, the kit comprising: a vessel formed from a plurality of walls comprising at least one side wall and a base forming an internal space for holding a bioreaction mixture, a means to move said bioreaction mixture, and one or more modules, said module comprising a housing and a transmitter disposed within said housing, said transmitter being capable of emitting one or more electromagnetic fields, wherein location means are provided to allow the one or more modules to be positioned proximal to at least one portion of said walls made from a material which is substantially transparent to said one or more electromagnetic fields, and/or wherein the one or more modules are disposed in the said internal space.

In one embodiment the vessel is formed by a frame and a sheet material supported on the frame so as to form said inner space.

In one embodiment said kit includes a plurality of modules and said modules are adapted and/or locatable so as to allow said modules to be located in a spaced array with respect to the said bioreaction mixture.

In one embodiment the kit includes agitating means to move the bioreaction mixture during the transmission of the one or more electromagnetic fields.

In a further aspect of the invention there is provided a module to emit one or more electromagnetic fields, said module including a housing, a power source, a transmitter to emit one or more electromagnetic fields and control means to allow the control of said one or more electromagnetic fields and wherein the one or more electromagnetic fields are controllable such that over a period of time they are emitted at; a predetermined frequency or a range of predetermined frequencies and are emitted continuously or as a series of pulses with a gap between said pulses of emission and said module locatable in, or in proximity to a bioreaction mixture such that at least part of the bioreaction mixture lies in range of the emitted one or more electromagnetic fields.

In a further aspect of the invention there is provided a method for improving the yield and/or acceleration and/or quality of a bioreaction, the method comprising the steps of: providing a vessel formed from a plurality of walls comprising at least one side wall and a base forming an internal space for holding a bioreaction mixture, moving said bioreaction mixture in said internal space, and providing one or more modules, said module comprising a housing and a transmitter disposed within said housing, said transmitter being capable of emitting one or more electromagnetic fields, emitting said one or more electromagnetic fields from said one or more modules into at least a portion of the internal space; and wherein the one or more modules are proximal to at least one portion of said walls made from a material which is substantially transparent to said one or more electromagnetic fields, and/or wherein the one or more modules are disposed in the said internal space.

In one embodiment the method includes the step of introducing a cell-culture media into the internal space of the vessel and introducing one or more cells into the cell-culture media to form a bioreaction mixture. In one embodiment the cell-culture media includes water molecules. Typically the one or more electromagnetic fields are emitted at a frequency to rotate the said water molecules and modulate the same.

In one embodiment the bioreaction mixture is moved during the application of the one or more electromagnetic fields.

In one embodiment the method includes the further step of applying one or more electromagnetic fields to cell-culture media prior to the introduction of the one or more cells thereto.

In one embodiment the emitting of the one or more electromagnetic fields includes applying pulsed electromagnetic fields to the bioreaction mixture.

In one embodiment the one or more electromagnetic fields have a frequency between 2.4 to 2.5 GHz and/or is emitted in pulses in the range of 0.5-1.5 milliseconds (ms) in duration and/or the said pulses are spaced apart by rest periods which are in the range of 40-66 ms and/or the pulses are emitted within a range of 12-20 pulses per second.

In one embodiment the one or more cells are yeast cells, and the bioreaction is for the production of bio-ethanol.

In one embodiment the one or more cells are mammalian cells, and the bioreaction is for the production of nucleic acids or peptides.

In one embodiment the one or more cells are hybridoma cells.

In one embodiment the one or more cells are insect cells, and the bioreaction is for the production of nucleic acids or peptides.

In one embodiment a plurality of modules are provided and located in an array.

In one embodiment the use of the at least one module is disabled until a payment has been made by a proposed user of the module to a module provider.

In one embodiment the payment which is made is equated to a number of switching on/off functions of the module and/or for a specific period of time of use of said module.

In one embodiment the user of the module selectively activates the module via a remote payment scheme and when payment has been made control means change the condition of the module, depending on the level of payment that has been made, to an active mode in which the one or more electromagnetic fields can be emitted therefrom.

In one embodiment the period of time of emission of the one or more electromagnetic fields is equivalent to all or part of the time for which the said bioreaction mixture is held in the inner space.

In one embodiment the electromagnetic fields are emitted in pulses.

Figure 2:
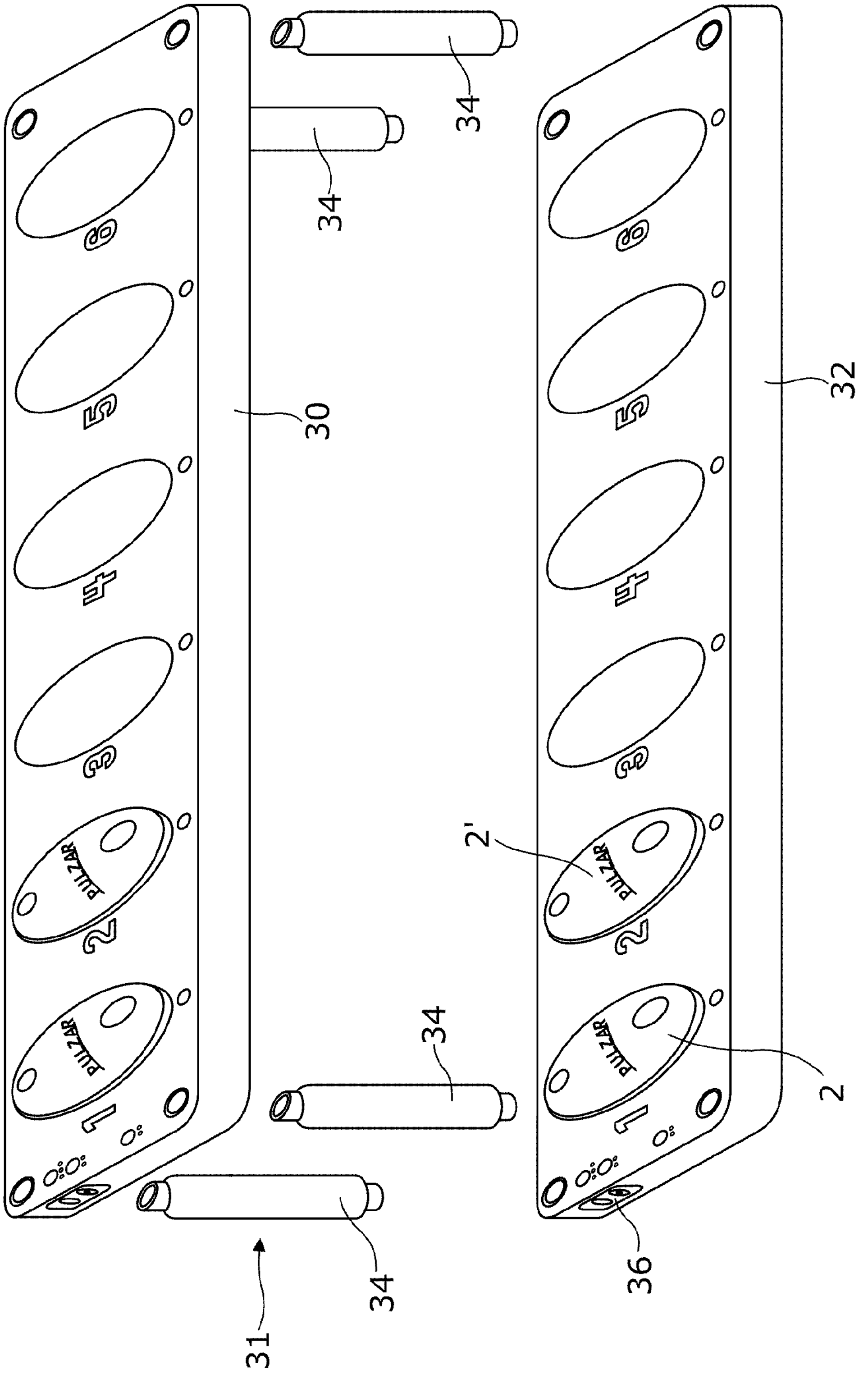
Figure 3B:
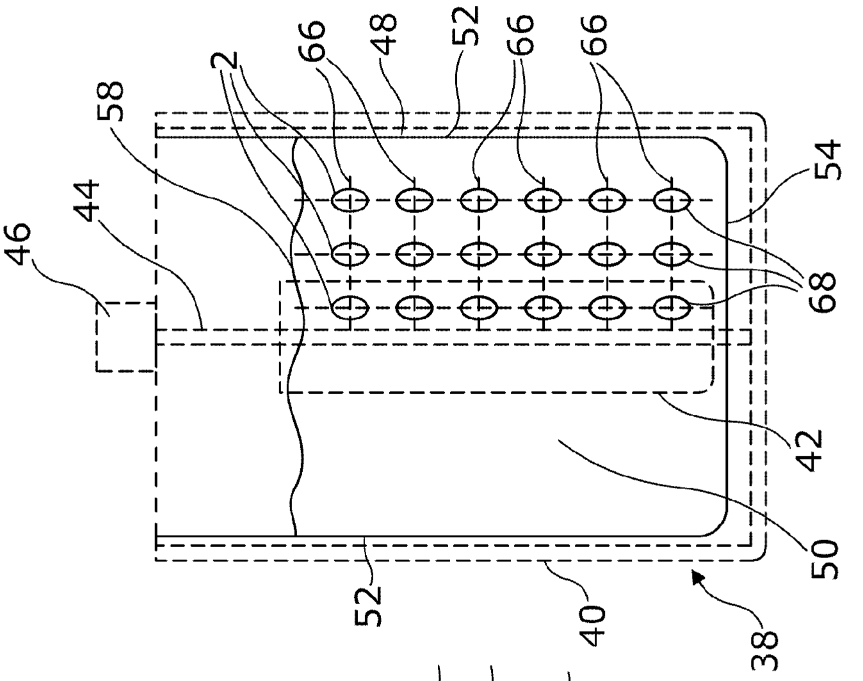
Figure 3C:
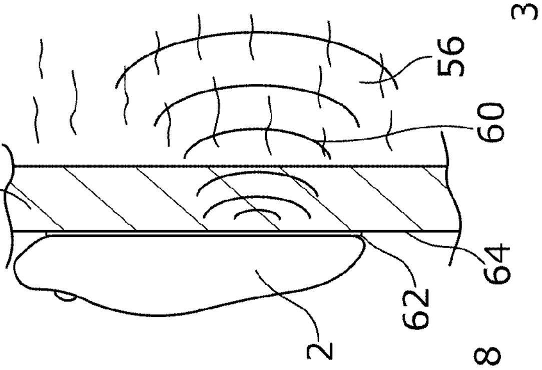
Figure 3A:
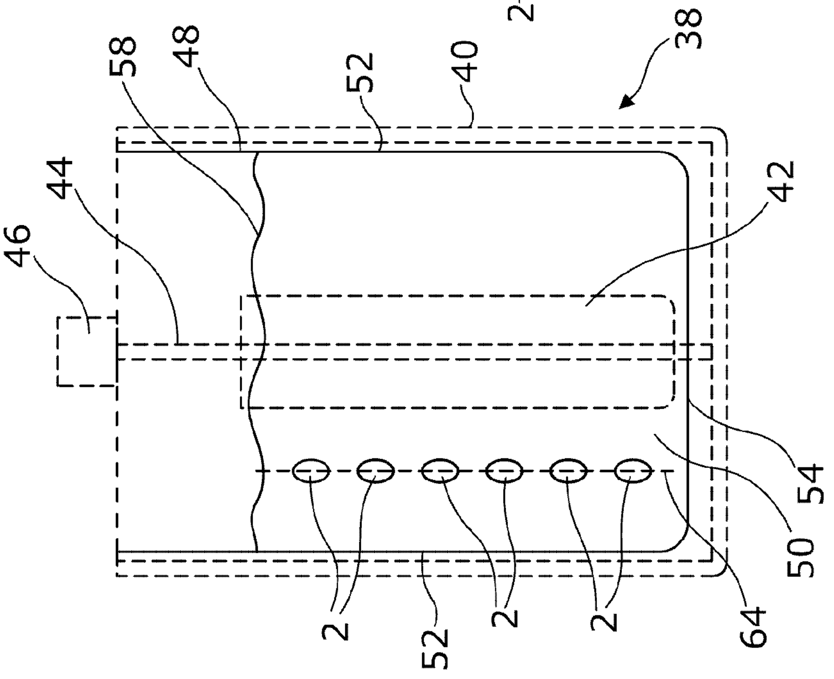
Figure 4:
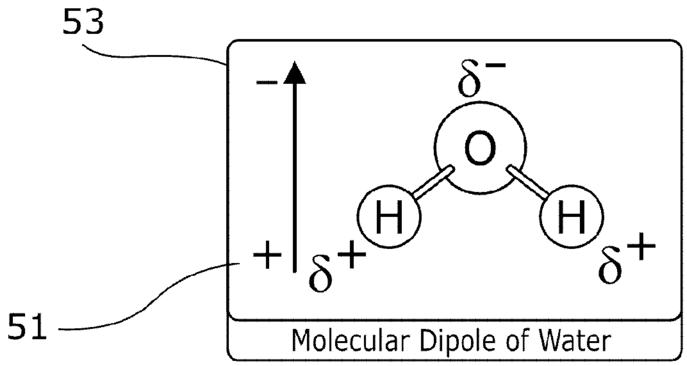
Figure 5:
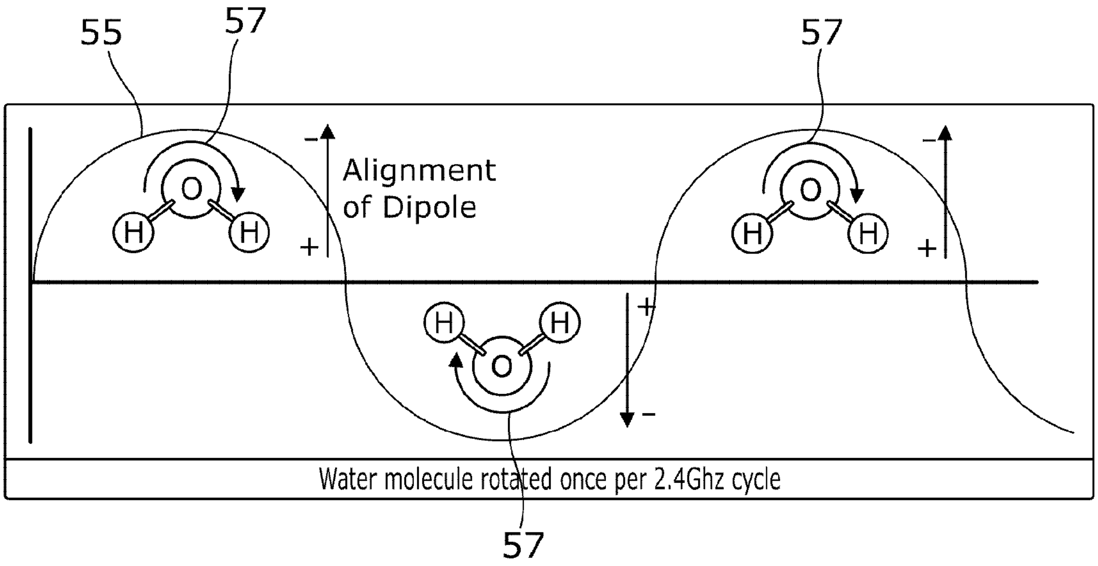
Figure 7A:
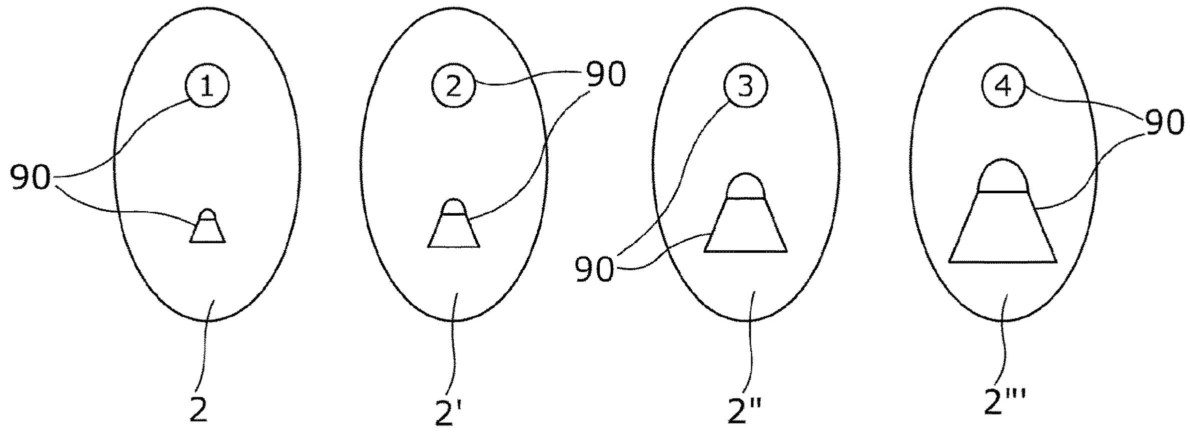

Specific embodiments of the invention are now described with reference to the accompanying drawings; wherein FIGS. 1*a-e* illustrates an embodiment of a module in accordance with one embodiment of the invention;

FIG. 2 illustrates a charging and/or control station or bank in accordance with one embodiment of the invention;

FIGS. 3*a-c* illustrate embodiments of use of the modules of FIGS. 1*a-e* in conjunction with a bioreactor vessel;

FIGS. 4 and 5 illustrate the rotation of the dipole of water when exposed to the electromagnetic fields emitted in accordance with the invention;

FIGS. 6*a-d* illustrate apparatus and results from experiments performed in accordance with the invention utilising a Chinese Hamster Ovary (CHO) cell line and with respect to IgG production;

FIGS. 7*a* and *b* illustrate a further embodiment of the invention; and

Figure 8A:
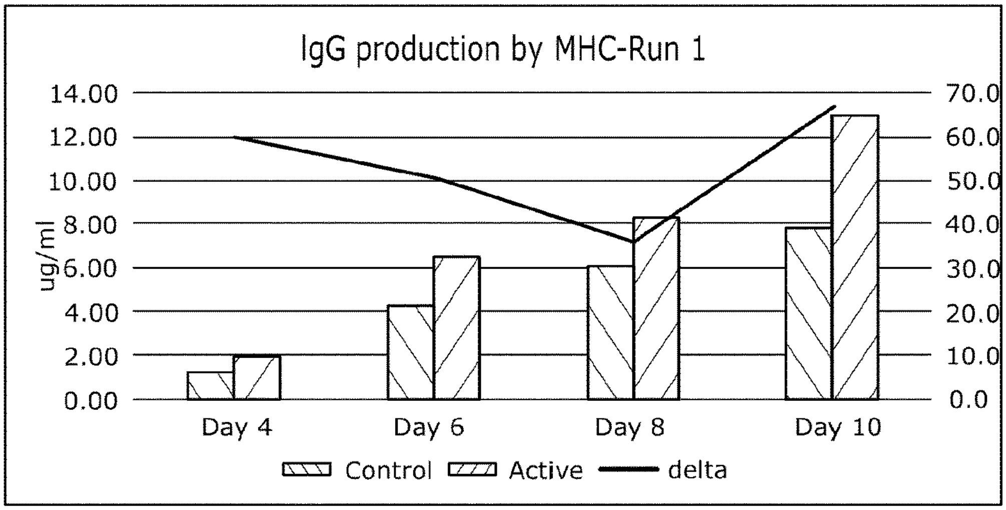
Figure 8B:
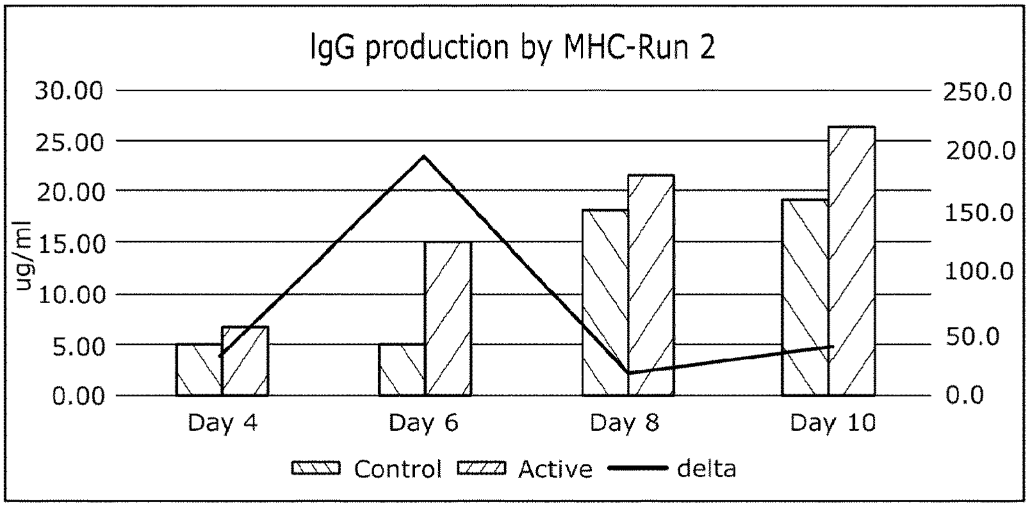
Figure 8C:
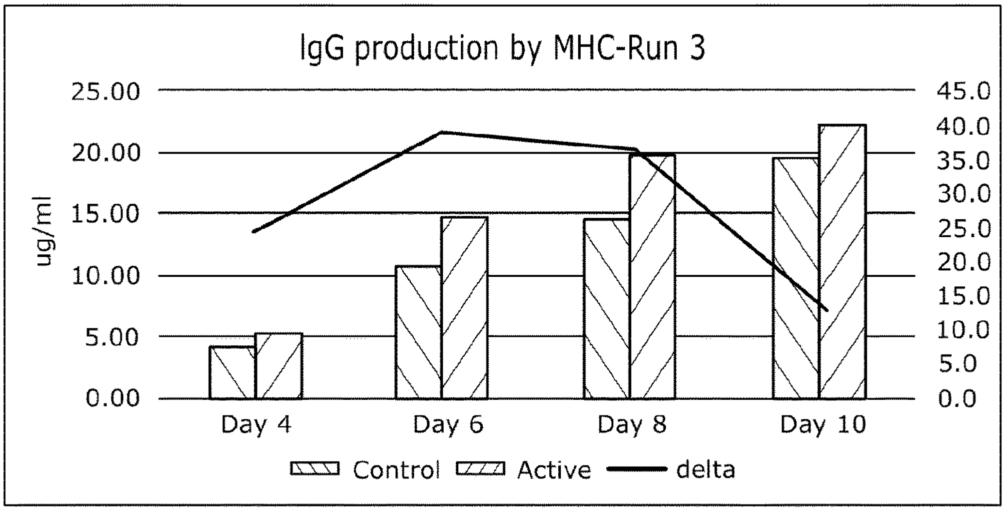

FIGS. 8*a-c* illustrate graphically results obtained from a further set of experiments using a Murine Hybridoma Cell (MHC) line and with respect to IgG production.

Referring firstly to FIGS. 1*a-e* there is illustrated a module 2 in accordance with one embodiment of the invention. In this embodiment the module 2 includes first and second parts 4,6 which, when attached together as indicated by arrows 8 in FIG. 1*d*, form an outer housing 10 which typically has a waterproof and dust proof seal. The housing may be provided with suitable sealing means depending upon the particular format of the same and the intended use of the same. In the embodiment shown there is an aperture 12 in the part 4 for the location of a button 14 which can be pressed down to operate an on/off switch 16 to activate or deactivate the module. A further aperture or zone 22 may be provided to indicate the location of emission of the electromagnetic fields and/or allow improved emission of the electromagnetic fields from the module transmitter 20 provided on printed circuit board 18 internally of the housing. Typically one transmitter will be provided per housing and module but it should be appreciated that in other embodiments one housing may have a series of transmitters located therein.

Figure 1E:
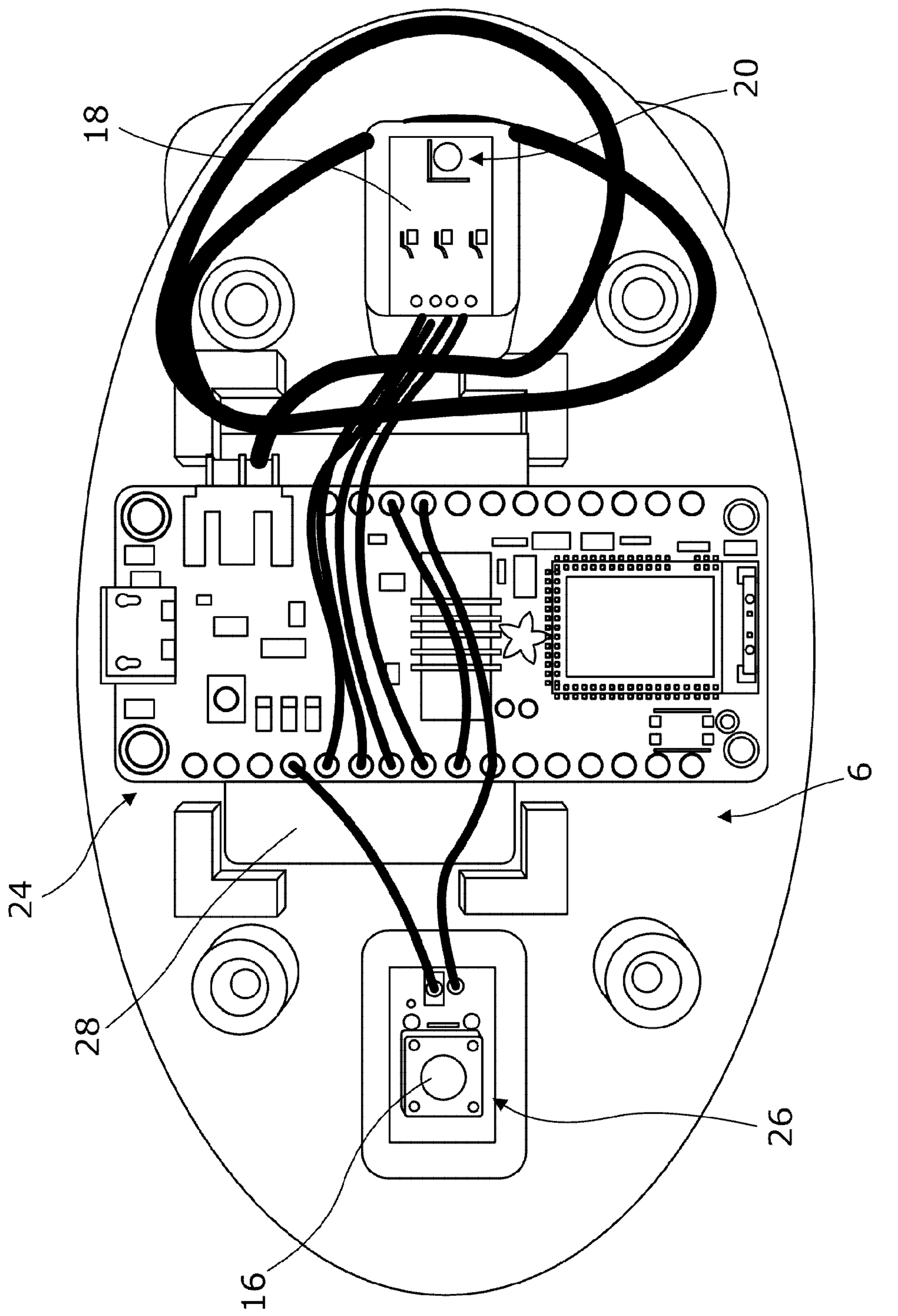

The printed circuit boards 18, 24, 26 are all located within the housing when formed and in this embodiment are held in location by means provided on the part 6 as shown in FIG. 1*e*. The main PCB 24 includes the control means components for the operation of the module 2 to control use of the power cell 28 and the frequency or frequencies and continuous or pulsed emission of the electromagnetic fields for a required period of time. The electromagnetic fields which are emitted in terms of frequency and/or continuous or pulsed electromagnetic fields may vary depending on the particular desired use of the modules at an instant of time. In one embodiment the module may include a receiver to allow the reception of control signals to update and/or alter the operation of the module and/or charge the module 2.

In one embodiment charging of one or more power cells located within the housing may be performed at a centralised location to which the modules are returned after use or, alternatively can be performed at a remote location, such as the end user location via a station 31, an example of which is illustrated in FIG. 2. In this embodiment two locating units 30, 32 are shown and which are stackable via support legs 34.

In this embodiment each unit has a number of locations in this case 1-6, each for the location of a module therewith and two of the modules 2, 2' are shown in position. Each unit is provided for connection 36 to a power supply and at each location 1-6 there is provided a wireless charging facility such that when the module is in position therewith the power source 28 within the same is wirelessly charged. Furthermore, each of the locations can be provided with a means to allow data connection with the control means components within the module to allow the control means for the module to be updated. In one embodiment the updating can be with respect to a new version of control software and/or to allow the module to be usable. In this latter case the activation may be achieved by the user making a payment, perhaps via the internet or an app, or by another means and the payment allows a signal to be sent to the units to allow one, some, or all of the modules to be rendered active and usable for a predetermined time or number of uses.

FIGS. 3*a* and *b* illustrate two embodiments of the apparatus in use. In both embodiments there is shown in a schematic manner a bioreactor vessel 38 which in these embodiments, includes a support frame 40 shown in broken lines, and which includes a means for moving a bioreaction mixture within an inner space of the vessel and in this embodiment the means for moving is an agitating stirrer 42, also shown in broken lines, which is provided for rotation around shaft 44 via motor 46. Also shown is the formation of the walls of the vessel by a, typically single use, plastic sheet material bag 48 which is supported by the frame and the bag has a plurality of walls including side walls 52 and a base 54, to define an inner space 50 in which the bioreaction mixture is held. Within the inner space 50 there is provided the bioreaction mixture 56 which is provided to a level 58 and can be moved around the inner space by the stirrer 42. Additional nutrients and/or other materials can be selectively added to the bioreaction mixture 56 during the process.

Also provided, in accordance with the invention, are a plurality of the modules 2 and in the two embodiments shown the plurality of modules 2 are provided so that, in conjunction, they can emit the one or more electromagnetic fields 60 through at least one wall, in the embodiments shown, side wall 52 of the bag 48 and into the bioreaction mixture 56 to at least create zones of electromagnetic fields through which the bioreaction mixture can be moved, and moved for a period of times which is at least part of the overall processing time for the bioreaction mixture. As illustrated in FIG. 3*c* with a module 2 being shown as located, in this embodiment by an adhesive layer 62 to the external surface 64 of the side wall 52. Alternatively, or in addition, mechanical location means are used to locate the module in position.

As an alternative to locating the module directly on the wall of the vessel the module may be located at a distance from the wall but sufficiently proximal so that the one or more electromagnetic fields emitted therefrom can pass through the wall and into the inner space so at allow the exposure of the bioreaction mixture thereto.

In FIG. 3*a* the modules 2 are provided in an array configuration in the form of a column along the axis 64 and typically to a height which matches the top level 58 of the bioreaction mixture 56 in the inner space 50. In FIG. 3*b* the array configuration provides a series of modules located along horizontal axes 66 and vertical axes 68 and it will be appreciated that the number of modules, the configuration of the array of the same and the operating parameters of the same will typically be predetermined with respect to the bioreaction mixture to be processed, the quantity of the bioreaction mixture, size of the reactor vessel and/or the required processing which is required to be performed.

In whichever embodiment, once the processing has been completed the modules can be removed and then reused immediately or passed for recycling and/or recharging and/or reprogramming as appropriate.

Typically, the electromagnetic fields are emitted in a range of 2.4-2.5 GHz which is an electronic frequency that when emitted into a bioreaction mixture liquid including water, $H_2O$, which has a molecular dipole of positive 51 and negative 53 as shown in FIG. 4, rotates the dipoles 51, 53, as illustrated in FIG. 5. As at least some of the water molecules are caused to rotate 57, typically one revolution per 2.4-2.5 GHz cycle, the hydrogen H bonds are broken and reformed so that this creates a wave of disturbance around hydrated surfaces of the bioreaction mixture which is being treated, such as cell membranes. This gives rise, amongst other effects, to increased fluidity around the membrane and an improved interface with the aqueous medium and hence allows the improved quality and/or yield and/or acceleration of the process. The emission of the electromagnetic fields in the said frequency range causes modulation of the electric field component of the electromagnetic wave 55 and the matching of the frequency range of the one or more electromagnetic fields so that the time for the hydrogen bonds to be broken corresponds to half a cycle of the frequency in the range of 2.4-2.5 GHz of the water molecules. The rate of change may also be affected by the temperature of the bioreaction mixture.

In tests, the apparatus and method have been applied to the use of expression of ethanol from yeast, and have a radical beneficial effect on yeast cells (eukaryotic cells). Pressure transducers convert the evolution of $CO_2$ into relative quantities of ethanol from which it is clear that the emission of the electromagnetic fields using the modules as herein defined not only doubles the rate of ethanol production but could also add to the total quantity of ethanol when the process is left to its conclusion.

Other uses include Nucleic acid transfection efficiency improvements, IgG Antibody yield improvement in mammalian cell lines, industrial application to single-use bioreactors (using the beneficial nature of plastic sheet material liners being transparent to the electromagnetic fields), enhancement of therapeutic protein production from yeast and application in which modules are used with conventional bioreactors.

Figure 6A:
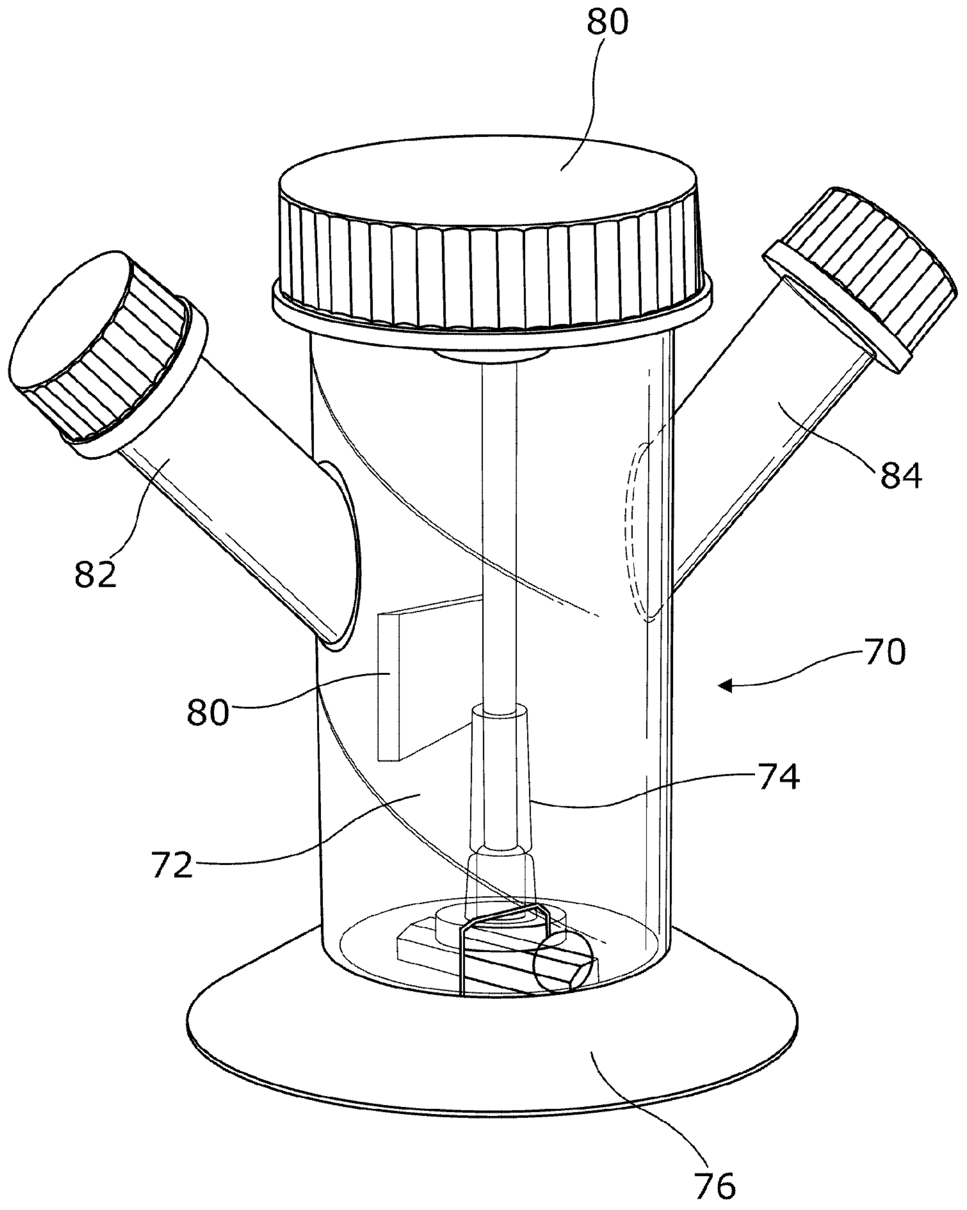

In tests undertaken utilising a module of the type shown in FIGS. 1*a-e*, a bioreactor vessel from "Corning®" in the form of a disposable spinner flask, P/N: CLS3152 with a 125 mL volume provided by Sigma Aldrich, USA was used. The vessel 70 is illustrated in FIG. 6*a* and has an inner space 72, with an agitating stirrer 74 therein, a base 76, top or lid 78 and side walls 80 and connecting passages 82, 84. The bioreaction mixture included cell culture and was located within the inner space 72 in the experiments. More specifically, the material in this set of experiments was a monoclonal IgG producing CHO cell line and the experiments studied the effects of the use of one module and the emission of the electromagnetic fields therefrom on the antibody production from the bioreaction mixture.

Figure 6B:
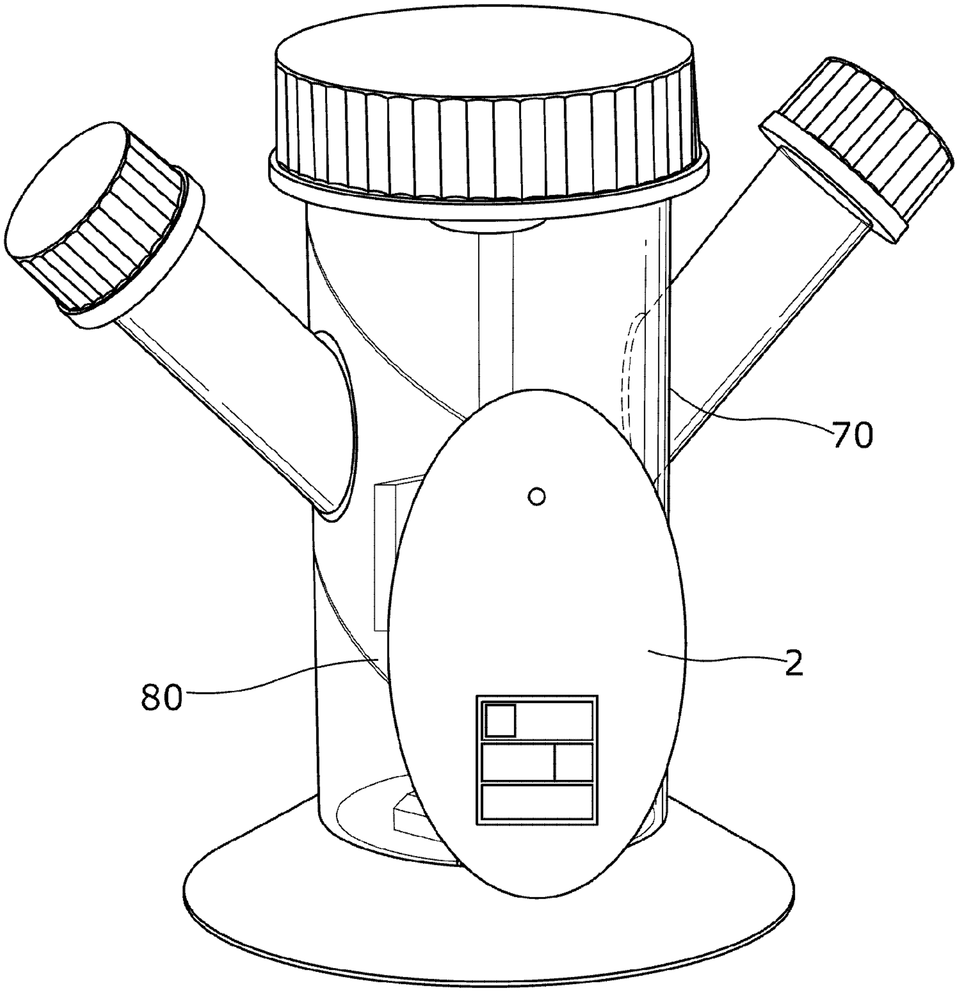

As shown in FIG. 6*b*, a module 2 in accordance with the invention, was located on the external face of the side wall 80 of the vessel and located with respect to the bioreaction mixture to be processed internally of the side wall in the inner space.

The module 2 included one transmitter for the electromagnetic fields.

Two versions of the experiment were undertaken, a first version (1) in which a module 2 in according with the invention was located at the location shown in FIG. 6*b* on the vessel 70 and a second, control, version (2) in which a dummy device which comprised the module housing 4 only, with no components so that there was no ability to transmit electromagnetic fields therefrom, was provided at the same location as the module 2 in version 1, with the vessel 70. The module 2 was switched on at the start of each experiment (Day 0) and placed in the said location. Sampling of the antibody yields which were achieved from experiment versions 1 and 2 of the experiments were undertaken at days 4, 6, 8 and 10 after switching on of the module.

Figure 6C:
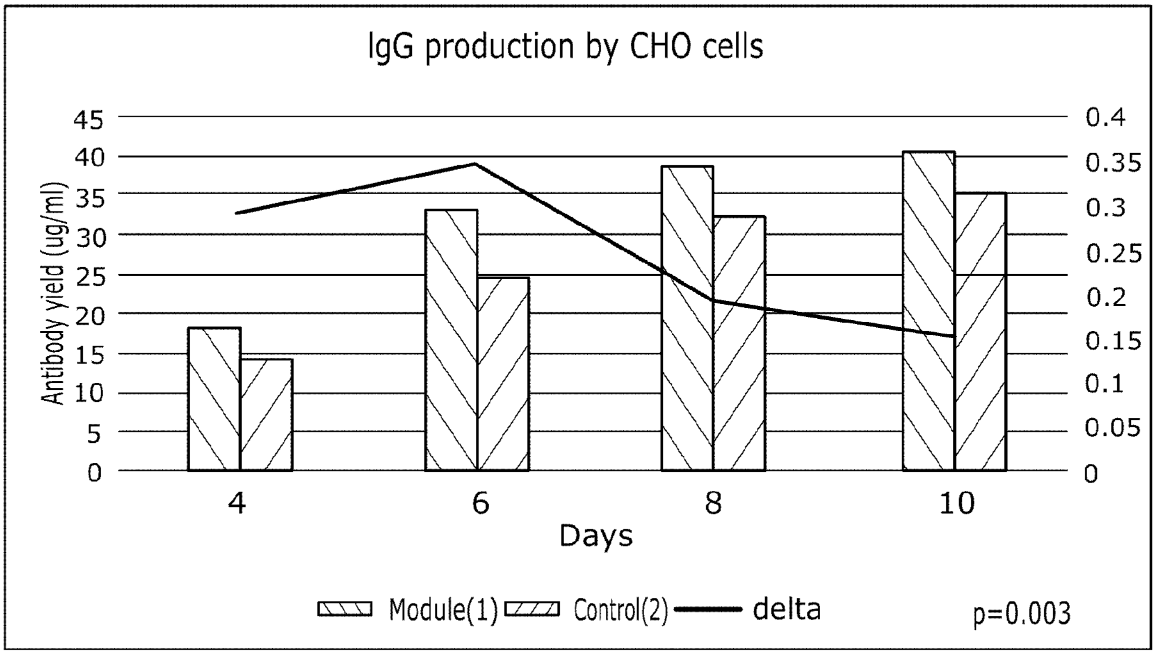

The average results of a campaign of experiments (n=6) are shown below in Table 1 and graphically in FIG. 6*c*.

| Average Yield | | | | ST. ER. | ST. ER. |
|---|---|---|---|---|---|
| Day post set up | Module(1) | Control(2) | delta | Mean Module (1) | Mean Control (2) |
| 4 | 18.438 | 14.272 | 0.292 | 3.259420802 | 2.294948094 |
| 6 | 33.171 | 24.610 | 0.348 | 3.30653162 | 3.632320054 |
| 8 | 38.715 | 32.355 | 0.197 | 4.308675478 | 4.632898692 |
| 10 | 40.608 | 35.137 | 0.156 | 2.662343771 | 2.516541155 |
| ttest | 0.003 | | | | |

A higher antibody yield was observed on each sampling day of experiment version 1 using the module 2 in comparison to the control experiment version 2, with a delta of 29%, 35%, 20% and 16% for days 4, 6, 8 and 10 respectively. A p-value of 0.003 calculated between the Module (1) experiment version and Control (2) experiment version throughout the 10 day period showed that the yield increase is statistically significant and therefore the use of the module 2 to emit the electromagnetic fields is statistically and experimentally verified to increase the yield of antibodies.

Figure 6D:
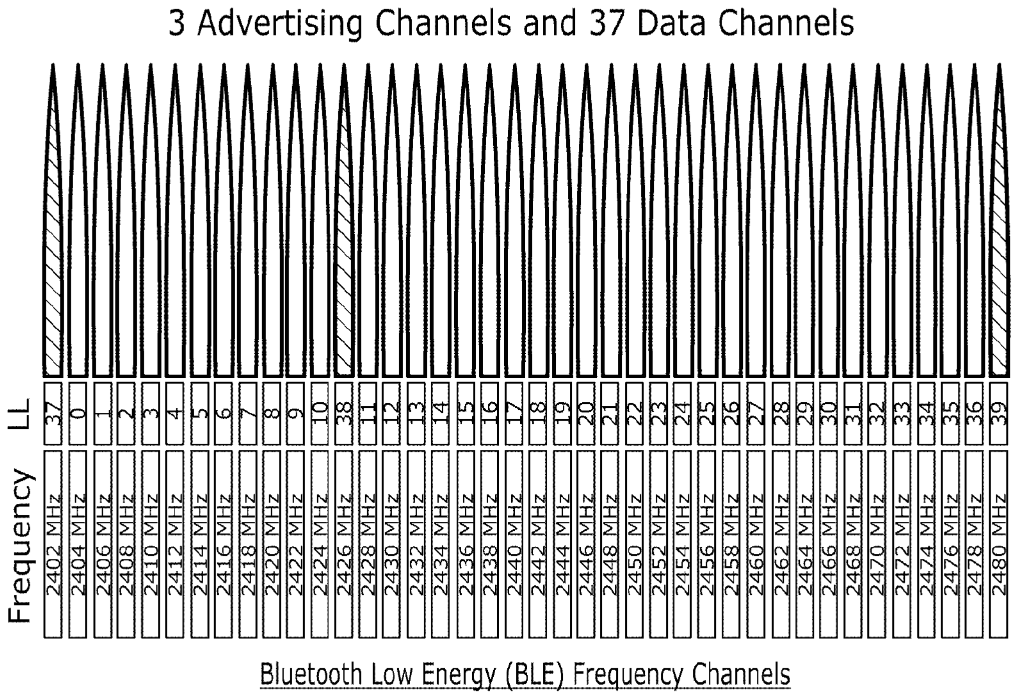

In this experiment the electromagnetic fields were emitted in a pulsed manner from the module 2 and the frequency of the emitted one or more electromagnetic fields was varied during the operation of the module over the predetermined period of time. In the experiment the electromagnetic fields were emitted at three different frequencies in a random sequence and these were 2402 MHz, 2426 Mhz, and 2480 MHz which are equivalent to Bluetooth emission protocol channels 37, 38 and 39 as illustrated in FIG. 6*d*.

The specific sequence of emission of the different frequencies, was random over the time period of operation of the module with the random delay of 0-10 milliseconds.

Further experiments were performed using a Murine Hybridoma Cell (MHC) line and the effect of the current invention in relation to the same on IgG production. The average of the results obtained in terms of cell counts, viability and yield for each of three runs using the invention (Version 1) are provided in the table below and graphically in FIGS. 8*a-c* and in comparison to a control test run (Version 2) performed on an identical culture but not using a module in accordance with the invention and in the same manner and locations using the same apparatus as set out with respect to the experiments described in relation to FIGS. 6*a-b*.

TABLE 2

| | Antibody yield | | | | | |
|---|---|---|---|---|---|---|
| | Experiment run1 | | Experiment run2 | | Experiment run3 | |
| | Control(2) | Active(1) | Control(2) | Active(1) | Control(2) | Active(1) |
| Day 4 | 1.27 | 2.02 | 4.91 | 6.54 | 4.17 | 5.20 |
| Day 6 | 4.28 | 6.46 | 5.00 | 14.85 | 10.69 | 14.88 |
| Day 8 | 6.12 | 8.30 | 18.20 | 21.63 | 14.52 | 19.81 |

TABLE 2-continued

| | Antibody yield | | | | | |
|---|---|---|---|---|---|---|
| | Experiment run1 | | Experiment run2 | | Experiment run3 | |
| | Control(2) | Active(1) | Control(2) | Active(1) | Control(2) | Active(1) |
| Day 10 | 7.81 | 12.98 | 19.22 | 26.61 | 19.65 | 22.22 |
| delta | 59.4 | | 33.1 | | 24.7 | |
| | 50.8 | | 197.0 | | 39.1 | |
| | 35.6 | | 18.8 | | 36.5 | |
| | 66.2 | | 38.4 | | 13.1 | |

In the results there is an increased viability and slowing of cell growth using the module which leads to an increase in level of production by the cells and thereby an increase in cumulative yield. On average over the three controlled experiments, the use of the module 2 gave rise to a 30% increase in IgG antibody yield in comparison to the conventional control results.

This increased production rate can be exemplified by comparing the day-8 yield to day 10 and the use of the modules achieved a higher yield.

At every time point throughout the experiments, the measured yield of antibody in the version 1 results in accordance with the invention arm was consistently higher than in the control version 2 and points to an increased antibody production rate. Moreover, this increased rate was achieved with a consistently lower number of total cells indicating that the observed productivity was a consequence of the higher sustained viability and higher productivity in the current invention.

In one embodiment the module can be operated continuously during the predetermined period of time or alternatively, the module is controlled to operate for a certain percentage of the said predetermined period of time, such as, for example 1 hour on and 3 hours off if the overall period of time of operation of the module is 4 hours so that the module is emitting one or more electromagnetic fields for 25% of the time.

Typically, the operation of the module to emit the one or more electromagnetic fields is pre-programmed and in one embodiment, can be updated either through the manual input of a change to the control system or via the transmission of new control system data potentially wirelessly.

In any case, the frequency of the electromagnetic fields and/or the selection of continuous or pulsed electromagnetic field emissions, is selected, and may vary, depending on the particular type of bioreaction mixture which is to be processed and exposed to the emitted one or more electromagnetic fields.

Figure 7B:
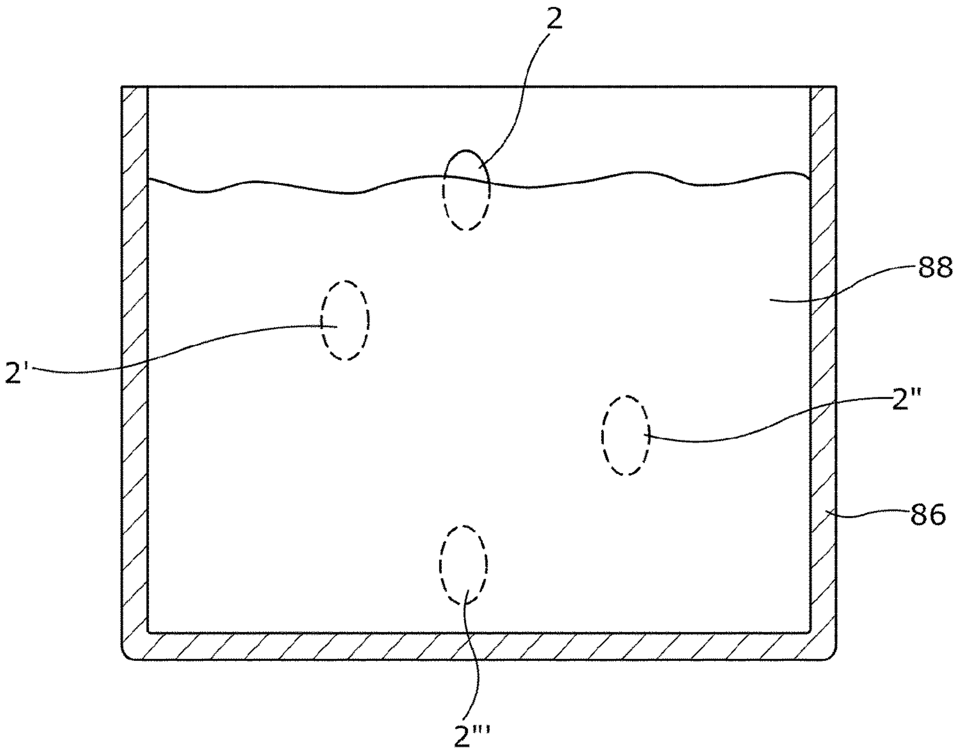

In a further embodiment of the invention, as described with regard to FIGS. 7*a*-*b*, instead of the modules being located proximal to a wall of the vessel 86, shown in broken lines, a plurality or group of modules 2, 2', 2", 2'" are positioned within the inner space of the vessel and in or partially in the bioreaction mixture which is to be exposed to the one or more electromagnetic fields. This arrangement is particularly useful where the bioreaction mixture 88 is in a relatively low turbulent condition i.e., no or little movement, such as by agitation of the bioreaction mixture is required such as, for example, if fermentation of the bioreaction mixture is the process. In this embodiment, the modules 2 are provided with components as previously described and, the housing 4 is provided with a liquid tight seal so as to prevent the bioreaction mixture 88 which is being processed, from entering the interior cavity of the module. The modules 2, 2', 2", 2'" are adapted so that when placed into the bioreaction mixture 88 they will move to different depths within the bioreaction mixture, as illustrated in FIG. 7*b* due to the modules having different intermediate buoyancy properties or values. The different properties or values are typically achieved by placing different quantities of a weight material, or the same quantities of different types of material with different weights in, or on, the modules. The different intermediate buoyancy levels are therefore used to ensure that when a group of the modules are placed into the bioreaction mixture, the same lie at different depths within the bioreaction mixture so that the electromagnetic fields which are emitted therefrom, are emitted at different locations within the bioreaction mixture so as to ensure that a substantially uniform exposure of the bioreaction mixture to the electromagnetic fields is achieved.

This in turn, means that the user of the group, can simply place all the modules, or a selected number of the modules depending on the depth of the bioreaction mixture which is being processed, into the bioreaction mixture and be sure that by placing the appropriate modules into the bioreaction mixture, then the substantially uniform exposure to the electromagnetic fields extends throughout the bioreaction mixture from the top surface to the bottom.

In one embodiment, the said modules include indication means 90, typically on the external surface of the housing, so as to identify, the modules and the grading of the buoyancy of the modules in the group as shown in FIG. 7*a*.

When the modules are placed on the external surface of the container, then, while it may be preferred that the modules are placed along the one or more sidewalls of the container so as to ensure substantially uniform exposure of the bioreaction mixture within the inner space to the one or more electromagnetic fields which are emitted, in addition or alternatively, the modules may be positioned at the base and/or top wall or lid of the inner space and/or on channels or passages leading to or from the same.

In different embodiments the module can be operated continuously during the predetermined period of time or alternatively, the module is controlled to operate for a certain percentage of the said predetermined period of time, such as, for example 1 hour on and 3 hours off if the overall period of time of operation of the module is 4 hours so that the module is emitting the electromagnetic field or fields for 25% of the time.

Typically, the operation of the module to emit the electromagnetic fields, is pre-programmed and in one embodiment, can be updated either through the manual input of a change to the control system or via the transmission of new control system data, potentially wirelessly.

In any case, the frequency of the electromagnetic fields and/or the selection of continuous or pulsed electromagnetic field emissions, is selected, and may vary, depending on the particular type of bioreaction mixture which is to be processed and exposed to the emitted electromagnetic fields.

One of the key advantages of the current invention is that the modules are provided to be selectively located in positions which best suit the shape of the vessel and/or the bioreaction mixture which is to be processed at that time.

The invention claimed is:

1. An apparatus for improving yield and/or acceleration and/or quality of a bioreaction, the apparatus comprising:

a vessel formed from a plurality of walls comprising at least one side wall and a base forming an internal space within the vessel suitable for holding a bioreaction mixture, one or more agitators for inducing movement of the bioreaction mixture, and one or more modules, the one or more modules comprising a housing and each module comprising a transmitter disposed within the housing, the transmitter configured to emit pulsed electromagnetic fields at a plurality of emission frequencies in a range of 2.4-2.5 GHZ, wherein the one or more modules are located proximate to at least one portion of the plurality of walls of the vessel and the at least one portion is made from a material which is transmissive for the pulsed electromagnetic fields, and/or wherein the one or more modules are disposed in the internal space within the vessel, wherein the apparatus further comprises a controller for controlling the pulsed electromagnetic fields emitted from the one or more modules such that the pulsed electromagnetic fields are emitted from the one or more modules as a sequence of pulses having a plurality of different emission frequencies in the range of 2.4-2.5 GHZ and having a rest period between the pulses, and wherein the rest period is configured to allow activity generated in the bioreaction mixture by the pulses to relax and promote homogeneity of the bioreaction mixture such that clusters in the bioreaction mixture are broken apart and an open structure of the bioreaction mixture is formed.

2. The apparatus according to claim 1, wherein the one or more agitators are one or more electrical and/or mechanical components and comprise any, or any combination of: an agitator within the vessel's internal space; an agitator external to the vessel's internal space; a wave generator; an actuator causing an input flow of material into the vessel's internal space and/or an actuator causing an output flow of material from the vessel's internal space.

3. The apparatus according to claim 1, wherein the one or modules are included with, attached to, or integral with the one or more agitators.

4. The apparatus according to claim 1, wherein the one or more agitators move the bioreaction mixture so as to periodically expose substantially all of the bioreaction mixture to the electromagnetic fields emitted from the one or more modules and/or to retain cells in the bioreaction mixture substantially in suspension in the bioreaction mixture.

5. The apparatus according to claim 1, wherein the apparatus further comprises a frame, and the vessel is a bag made from a flexible, resilient, plastic material and is supported by the frame.

6. The apparatus according to claim 1, wherein the bioreaction mixture includes water, and the electromagnetic fields are emitted at a frequency so as to cause rotation of molecular dipoles of water contained in the bioreaction mixture.

7. The apparatus according to claim 1, wherein the electromagnetic fields are emitted at a plurality of different frequencies in a random sequence during a period of time.

8. The apparatus according to claim 1, wherein, when there are two or more modules, wherein the controller controls allows the electromagnetic fields emitted therefrom to be emitted in a synchronised manner.

9. The apparatus according to claim 1, wherein the apparatus comprises one or more locators for locating the one or more modules proximate to, or within the vessel.

10. The apparatus according to claim 1, wherein the one or more modules are disposed in the vessel's internal space and further comprise at least one buoyancy portion for holding the one or more modules at a depth in the bioreaction mixture when the bioreaction mixture comprises a liquid.

11. The apparatus according to claim 10, wherein, when there are two or more modules, at least one module of the two or more modules has the at least one buoyancy portion to retain the at least one module at a different depth than another module or modules in the bioreaction mixture when the bioreaction mixture comprises a liquid.

12. The apparatus according to claim 1, wherein the one or more modules are two or more modules, and each of the two or more modules is located at a node of another module.

13. The apparatus according claim 1, wherein the one or more modules are two or more modules located in an array which extends along a single axis or is provided to extend along a plurality of axes.

14. The apparatus according to claim 13, wherein the two or more modules are located in the array with a spacing within a range of 5-10 cm between adjacent modules in the array.

15. The apparatus according to claim 13, wherein the two or more modules are located in the array with a spacing between adjacent modules of the array which is approximately equal to half a wavelength of an emission frequency.

16. The apparatus according to claim 15, wherein the spacing between the adjacent modules is between 5-10 cm.

17. The apparatus according to claim 1, wherein the one or more modules include a wireless receiver to allow reception of signals to cause a change in at least one operating parameter of the one or more modules to be transmitted wirelessly and received by the same, and implement the change.

18. The apparatus according to claim 1, wherein the apparatus includes a charging and/or control unit to which the one or more modules, when not in use, are connected electrically and/or data connected so as to allow charging and/or control of activation.

19. The apparatus according to claim 1, wherein the bioreaction mixture is any, or any combination of, a biofuel, cultures of genetically modified cells and organisms, insulin, monoclonal antibodies, growth hormones, interferon, interleukins, blood factor VIIa, blood factor VIII, blood factor IX, erythropoietin, gonadotrophin, glucagon, vaccine antigenic sequences, or mammalian cell culture.

20. The apparatus according to claim 1, wherein the rest period is between 25-140 times longer than a duration of the pulses.

21. A method for improving yield and/or acceleration and/or quality of a bioreaction using the apparatus according to claim 1, the method comprising steps of:

using the vessel formed from the plurality of walls comprising at least one side wall and the base forming the internal space for holding the bioreaction mixture, moving said bioreaction mixture in said internal space, emitting the pulsed electromagnetic fields from said one or more modules into at least a portion of the internal space; and wherein the one or more modules are proximate to at least one portion of said walls made from a material which is transmissive for the pulsed electromagnetic fields, and/or wherein the one or more modules are disposed in the internal space.

22. The method according to claim 21, wherein the method comprises a step of introducing a cell-culture media into the internal space of the vessel and introducing one or more cells into the cell-culture media to form the bioreaction mixture.

23. The method according to claim 22, wherein the bioreaction mixture is moved during application of the pulsed electromagnetic fields.

24. The method according to claim 22, further comprising a step of applying the pulsed electromagnetic fields to the cell-culture media prior to the introduction of the one or more cells thereto.

25. The method according to claim 22, wherein the one or more cells are yeast cells and the bioreaction is for the production of bio-ethanol, or the one or more cells are mammalian cells and the bioreaction is for the production of nucleic acids or peptides, or the one or more cells are hybridoma cells, or the one or more cells are insect cells and the bioreaction is for the production of nucleic acids or peptides.

26. The method according to claim 21, wherein the bioreaction mixture includes water, and the pulsed electromagnetic fields are emitted at a frequency to rotate water molecules and modulate the same.

27. The method according to claim 26, wherein an electric field component of a wave of the pulsed electromagnetic fields is modulated by matching a frequency range of the pulsed electromagnetic fields so that a time for hydrogen bonds to be broken substantially corresponds to half a cycle of a frequency of emission.

28. The method according to claim 21, wherein the pulsed electromagnetic fields are emitted as a series of pulses with the rest period between successive pulses.

29. The method according to claim 28, wherein the pulsed electromagnetic fields are emitted in pulses in a range of 0.5-1.5 milliseconds (ms) in duration, the pulses are spaced apart by rest periods which are in a range of 40-66 ms, and/or the pulses are emitted within a range of 12-20 pulses per second.

30. An apparatus for improving yield and/or acceleration and/or quality of a bioreaction, the apparatus comprising;

a vessel formed from a plurality of walls comprising at least one side wall and a base forming an internal space within the vessel suitable for holding a water-containing bioreaction mixture, one or more agitators for inducing movement of the water-containing bioreaction mixture, and one or more modules, the one or more modules comprising a housing and each module comprising a transmitter disposed within the housing, the transmitter configured to emit pulsed electromagnetic fields at a plurality of emission frequencies, wherein the one or more modules are located proximate to at least one portion of the plurality of walls of the vessel and the at least one portion is made from a material which is transmissive for the pulsed electromagnetic fields, and/or wherein the one or more modules are disposed in the internal space within the vessel, and wherein the apparatus further comprises a controller for controlling the pulsed electromagnetic fields emitted from the one or more modules such that the pulsed electromagnetic fields are emitted as a sequence of pulses having a plurality of different emission frequencies that cause rotation of molecular dipoles of water molecules contained in the water-containing bioreaction mixture and having a rest period between the pulses, and wherein the rest period is configured to allow activity generated in the water-containing bioreaction mixture by the pulses to relax and promote homogeneity of the water-containing bioreaction mixture such that clusters in the water-containing bioreaction mixture are broken apart and an open structure of the water-containing bioreaction mixture is formed.

31. The apparatus according to claim 30, wherein the rest period is between 25-140 times longer than a duration of the pulses.

32. The apparatus according to claim 30, wherein the one or more modules are two or more modules located in an array with a spacing between adjacent modules of the array which is approximately equal to half a wavelength of an emission frequency.

33. The apparatus according to claim 32, wherein the spacing between the adjacent modules is between 5-10 cm.

34. A method for improving yield and/or acceleration and/or quality of a bioreaction using the apparatus according to claim 30, the method comprising steps of:

using the one or more agitators to induce movement of the bioreaction mixture; and using the controller to control the pulsed electromagnetic fields emitted from the one or more modules such that the pulsed electromagnetic fields are emitted as a sequence of pulses having a plurality of different emission frequencies that cause rotation of molecular dipoles of water molecules contained in the water-containing bioreaction mixture and having a rest period between the pulses, and wherein the rest period is configured to allow activity generated in the bioreaction mixture by the pulses to relax and promote homogeneity of the bioreaction mixture such that clusters in the bioreaction mixture are broken apart and an open structure of the bioreaction mixture is formed.

* * * * *